(12) United States Patent
Itoh et al.

(10) Patent No.: US 6,864,975 B2
(45) Date of Patent: Mar. 8, 2005

(54) METHOD OF AND SYSTEM FOR ANALYZING A SAMPLE CONTAINING A PLURALITY OF FLUORESCENT SUBSTANCES

(75) Inventors: Kazuyoshi Itoh, Hyogo pref. (JP); Kiichi Fukui, Osaka pref. (JP); Kunihiko Ohkubo, Shiga pref. (JP)

(73) Assignee: Shimadzu Corporation, Kyoto (JP)

( * ) Notice: Subject to any disclaimer, the term of this patent is extended or adjusted under 35 U.S.C. 154(b) by 173 days.

(21) Appl. No.: 10/310,032

(22) Filed: Dec. 5, 2002

(65) Prior Publication Data

US 2003/0117618 A1 Jun. 26, 2003

(30) Foreign Application Priority Data

Dec. 6, 2001 (JP) ........................................ 2001-372570

(51) Int. Cl.⁷ ............................. G01N 21/64; G01J 3/18
(52) U.S. Cl. ........................ 356/317; 356/310; 356/330; 356/318; 250/458.1
(58) Field of Search ................................. 356/310, 326, 356/328, 330, 334, 317, 318; 250/458.1, 459.1, 461.1, 461.2

(56) References Cited

U.S. PATENT DOCUMENTS

| 4,807,993 A | 2/1989 | Nakamura et al. |
| 6,178,041 B1 | 1/2001 | Simon |
| 6,377,344 B2 * | 4/2002 | Schoeppe ................... 356/318 |

FOREIGN PATENT DOCUMENTS

| DE | 43 30 347 A | 3/1995 |
| DE | 199 30 532 A | 1/2001 |
| EP | 0 533 302 A1 | 3/1993 |
| GB | 2352827 A * | 2/2001 ........... G02B/21/00 |

OTHER PUBLICATIONS

Weiner A.M.: "Femtosecond Pulse Shaping Using Spatial Light Modulators", Review of Scientific Instruments, American Institute of Physics, New York, US, vol. 71, No. 5, May 2000 (pp. 1929–1960).

* cited by examiner

Primary Examiner—F. L. Evans
(74) Attorney, Agent, or Firm—Westerman, Hattori, Daniels & Adrian, LLP

(57) ABSTRACT

The present invention proposes a method of and system for analyzing samples (particularly, bio-samples), wherein the continuous spectrum white light pulse generated from an ultra-short optical pulse is used in a simple manner. By a system according to the invention, continuous spectrum white light pulses generated by converging ultra-short optical pulses on a point in a transparent substance 23 are dispersed into a spectrum of light by a dispersing element 25, and a plurality of objective wavelength components are separately selected by small reflection mirrors 37, masked mirrors or the like. The selected objective wavelength components are combined by the dispersing element 25 into a composite optical pulse containing the objective wavelength components. The composite optical pulse is irradiated onto the bio-sample 28 or other samples, whereby only the desired fluorescent substances are excited by the objective wavelength components corresponding to them. The selected objective wavelength components may preferably have different light path lengths. By this construction, the component optical pulses corresponding to the objective wavelengths in the composite optical pulse are separated from each other, so that the noise due to the interference of different wavelength components is prevented.

24 Claims, 8 Drawing Sheets

ND FILTER (FRONT VIEW)

METHOD OF AND SYSTEM FOR ANALYZING A SAMPLE CONTAINING A PLURALITY OF FLUORESCENT SUBSTANCES

The present invention relates to a method of and system for analyzing a sample by simultaneously exciting a plurality of fluorescent substances contained in the sample. The present invention will enable a simultaneous and independent tracing of motions and/or actions of a plurality of proteins or the like contained in a living body, because many proteins and other substances contained in living bodies are naturally fluorescent, or can be fluorescent using fluorescent probes.

BACKGROUND OF THE INVENTION

When ultra-short optical pulses of femtosecond ($10^{-15}$ second) order are spatially converged and irradiated onto a substance, the energy density at the irradiation point becomes so high as to induce linear and nonlinear interactions between the optical pulses and the substance. Various phenomena result from this interaction, one of which is the generation of a pulse of white light with a continuous spectrum (which is referred to as the "continuous spectrum white light pulse" hereinafter). The continuous spectrum white light pulse has a continuous spectrum while being an ultra-short pulse similar to the original pulse. Having such characteristics, the continuous spectrum white light pulse is expected to have various applications.

Figure 1:
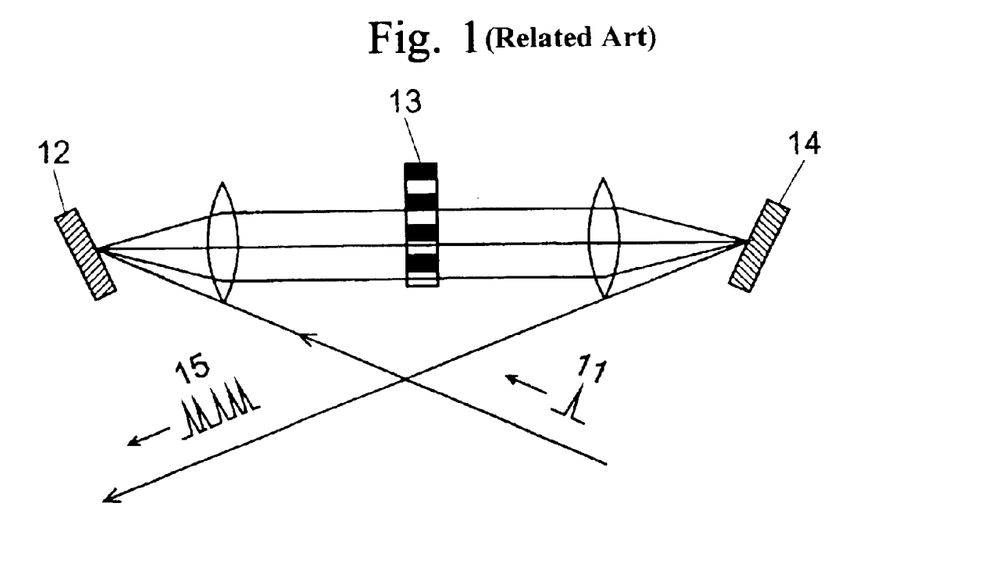
FIG. 1 shows the construction of a Fourier transformation system by Weiner.

An example of several possible applications is the generation of modulation pulse for the transmission of information (Jonathan P. Heritage, Andrew M. Weiner, "Shaping Optical Pulses by Amplitude and Phase Masking", U.S. Pat. No. 4,655,547, Apr. 7, 1987, Andrew M. Weiner, "Research Projects—Femtosecond Pulse Shaping and Processing", http://purcell. ecn.purdue.edu/~fsoptics/PulseShaping.html). As shown in FIG. 1, the continuous spectrum white light 11 generated from an ultra-short optical pulse is dispersed by a dispersing element 12, and the dispersed light passes through a mask 13 having different transmittances or phase shifters for different wavelength components. Then, a lens and a dispersing element 14 combine the light from the mask 13 into one pulse. Thus, a pulse 15 having a Fourier transformation pattern of the mask 13 is obtained.

The above-described method converts the spatial information represented by the mask into the temporal information represented by the pulses, which was invented as a technique for the transmission of information. Also, the relationship between the input (spatial information) and the output (temporal information) is very complex because it is a Fourier transformation, as explained above.

Thus, an objective of the present invention is to propose a method of and system for analyzing fluorescent samples (particularly, bio-samples), wherein the continuous spectrum white light pulse generated from ultra-short optical pulse is used in a simpler manner.

SUMMARY OF THE INVENTION

To solve the above problem, the present invention proposes a method of analyzing a sample, which includes:

a) a step wherein a continuous spectrum white light pulse generated from an ultra-short optical pulse is dispersed into a spectrum of light by a dispersing element;

b) a step wherein only a plurality of objective wavelength components are selected from the dispersed light;

c) a step wherein the plurality of objective wavelength components are combined by a reverse dispersing element into a composite optical pulse containing the objective wavelength components; and d) a step wherein the composite optical pulse is irradiated onto the sample to excite a plurality of objective fluorescent substances corresponding to the plurality of objective wavelength components.

In an improved method of the present invention, the selected plurality of objective wavelength components have different light path lengths so that the composite optical pulse contains its component optical pulses corresponding to the objective wavelength components with time differences.

Also, the present invention proposes a system for analyzing a sample, which includes:

a) a dispersing element for dispersing a continuous spectrum white light pulse generated from an ultra-short optical pulse into a spectrum of light;

b) a wavelength selection device for selecting only a plurality of objective wavelength components contained in the dispersed light;

c) a reverse dispersing element for combining the selected plurality of objective wavelength components into a composite optical pulse; and d) an irradiating optical system for irradiating the composite optical pulse onto the sample.

In the analysis according to the present invention, the user should first ascertain the frequencies necessary to excite the plurality of fluorescent substances under study. According to the present invention, since the excitation light is generated from an ultra-short optical pulse, a multiphoton excitation, such as two- or three-photon excitation, takes place. This fact should be taken into account in the selection of the excitation frequencies.

The excitation light, or the continuous spectrum white light pulse, is dispersed into a spectrum, from which only the plurality of excitation wavelength components (or objective wavelength components) are selected. Examples of the method of selecting objective wavelength components include: placing reflecting mirrors only at such positions that correspond to the objective wavelength components; using a reflecting mirror covered with an absorption cover except for the parts that reflect the objective wavelength components; and using a mask designed to pass the dispersed light only at such parts that correspond to the objective wavelength components.

The selected objective wavelength components are combined by a reverse dispersing element to generate a composite optical pulse. The reverse dispersing element may be newly provided in addition to the dispersing element used for generating the spectrum, or the dispersing element may be also used as the reverse dispersing element.

The composite optical pulse thus generated contains only such wavelength component pulses that excite the objective substances. Therefore, of various kinds of substances contained in the sample, only the desired fluorescent substances are excited by the composite optical pulse. Also, by the present invention, the composite optical pulse excites the fluorescent substances in the sample in a multiphoton excitation mode, such as a two- or three-photon excitation, because it is an ultra-short optical pulse similar to the original optical pulse. In normal excitation caused by linear absorption of photons, the absorption of light occurs at all the part where the light passes. On the other hand, in multiphoton excitation, the absorption non-linearly occurs only at around the focal point, so that information about the sample at around the focal point can be obtained. Two- or three-dimensional scanning of the focal point will provide a two- or three-dimensional analytic image. Further, tracing of the image with time will enable the observation of the motion or the like of the objective substances.

In the above-described method, it is possible that the components of the composite optical pulse generated by the reverse dispersing element interfere with each other, generating difference frequency components of light due to the non-linear effect. The difference frequency components thus generated may excite fluorescent substances other than the objective ones, which causes a noise in the analysis. Therefore, in an improvement of the present invention, the light path lengths of the objective wavelength components are made different from each other before the objective wavelength components are combined together. By this method, the component optical pulses are separately contained in the composite optical pulse, so that the difference frequency component and the above noise are prevented.

One method of giving differences in the light path lengths is to place small reflecting mirrors on the light paths of the objective wavelength components at different positions along the light paths. Another method is to place transparent optical media, each having a different thickness (i.e. the dimension in the direction of the light path), on the light paths of the objective wavelength components. The optical media should be preferably made from a material having a large refractive index.

The components of the dispersed light may be chirped, whereby the peak power of the wavelength components contained in the composite optical pulse can be changed. This method enables control of the absorption of light at an arbitrary level between the linear absorption and the non-linear (or multiphoton) absorption in the objective fluorescent substances.

Figure 2:
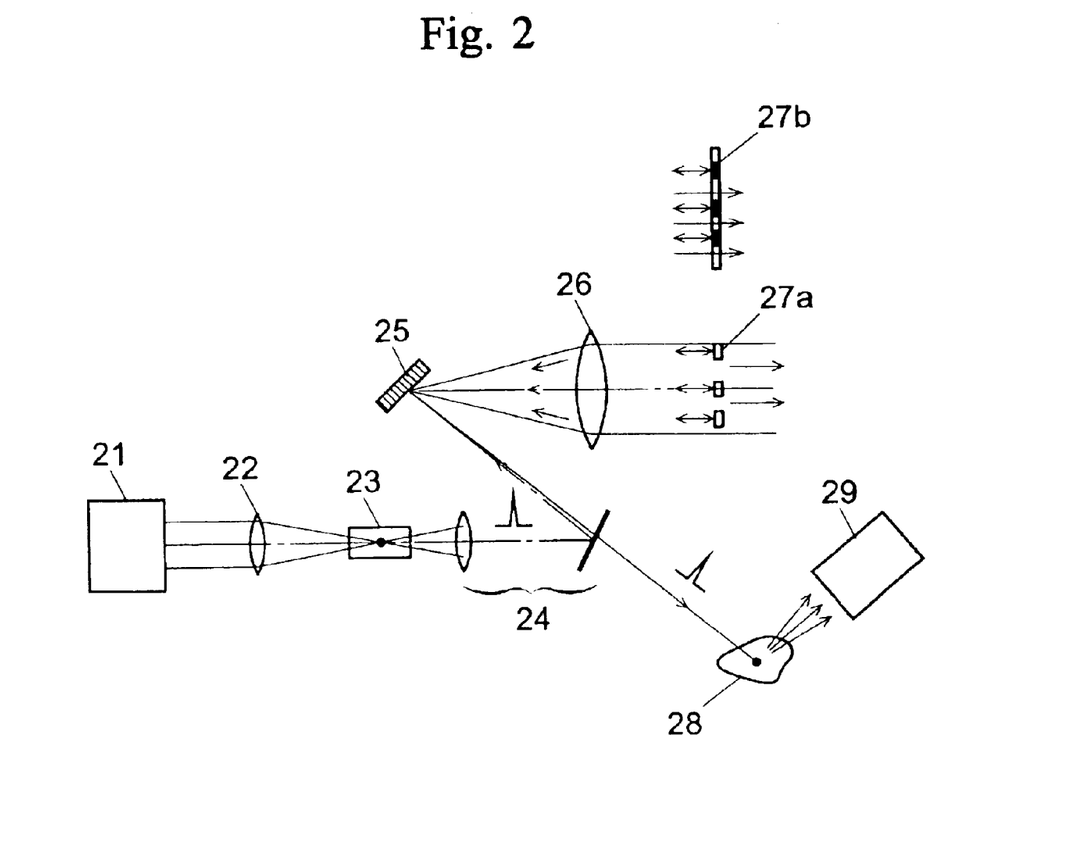
FIG. 2 shows the construction of an optical system for generating composite optical pulses for the analysis of a plurality of fluorescent substances according to the present invention.

FIG. 2 shows an example of a system for performing an analysis by a method according to the present invention. In FIG. 2, the light source 21 is, for example, an erbium-doped fiber laser, a mode-locked Ti:Sapphire laser or a mode-locked Cr:Forsterite laser (see U.S. Pat. No. 6,154,310), which generates an ultra-short optical pulse. The ultra-short optical pulse is converged by a first optical system 22 on a point in a transparent substance 23, such as water or quartz crystal, which forms, for example, an optical fiber. At the convergence point, a non-linear interaction occurs between the substance 23 and the ultra-short optical pulse, generating a continuous spectrum white light pulse. The continuous spectrum white light pulse enters a second optical system 24 including lenses, reflecting mirrors, etc. The second optical system 24 irradiates the pulse onto a dispersing element 25, which in turn disperses the pulse into a spectrum of light. The dispersed light enters a collimator 26, which sends the light to a wavelength selection device 27. FIG. 2 shows two types of wavelength selection device: the first type 27a includes small reflecting mirrors placed on the light paths of the objective wavelength components, and the second type 27b includes a reflecting mirror provided with light-absorbing parts at positions corresponding to wavelengths other than the objective ones.

Then, the collimator 26 sends the selected wavelength components back to the dispersing element 25, which in turn combines the wavelength components into an ultra-short optical pulse. The ultra-short optical pulse is irradiated onto the sample 28 to excite the plurality of objective substances. The fluorescence is detected by a detector 29.

Figure 3:
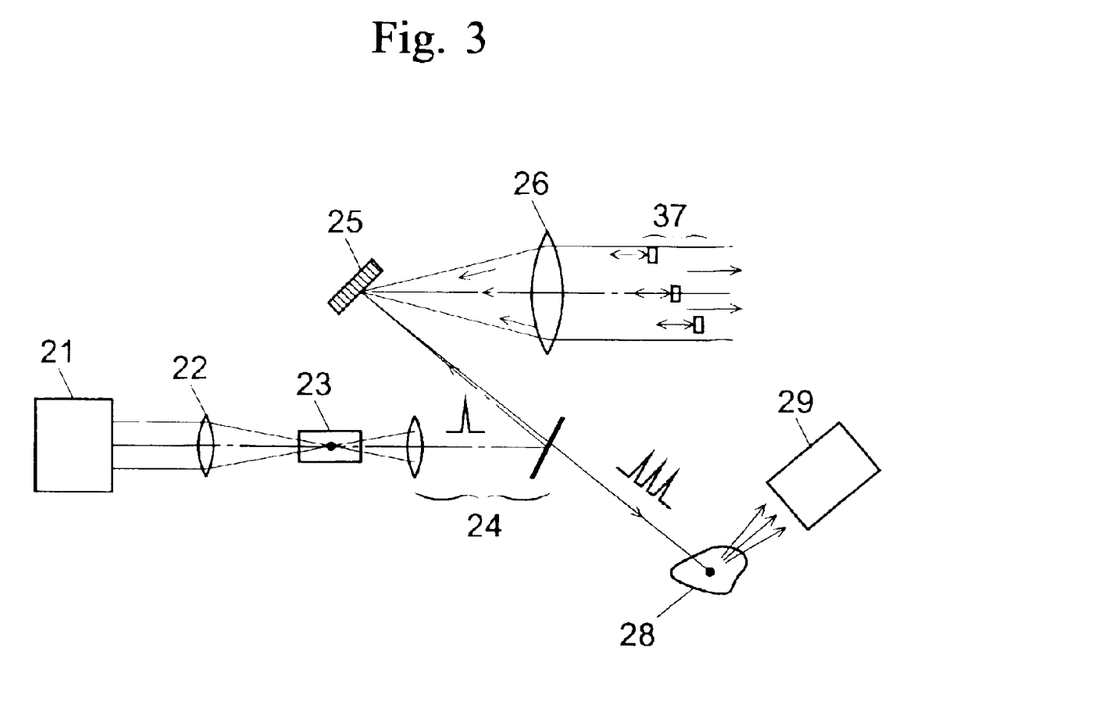
FIG. 3 shows the construction of an example of an optical pulse generating system for generating a composite optical pulse in which components of light are separated.
Figure 4:
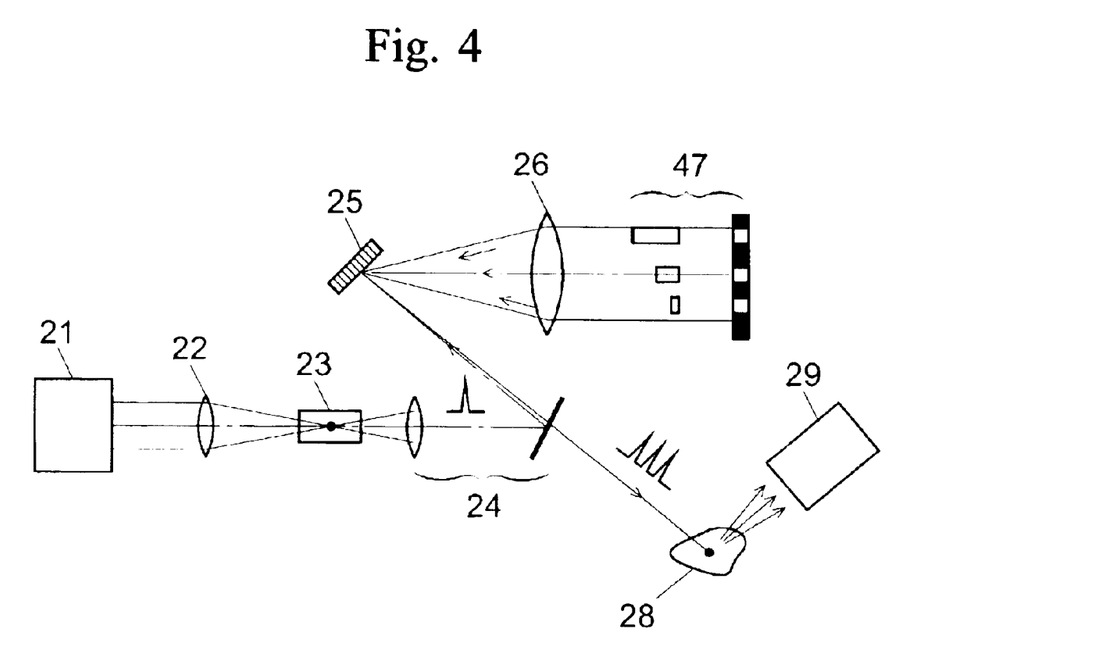
FIG. 4 shows the construction of another example of an optical pulse generating system for generating a composite optical pulse in which components of light are separated.

FIGS. 3 and 4 show examples of the system for giving different light path lengths to the components of the dispersed light. The system in FIG. 3 includes small reflecting mirrors 37 placed on the light paths of the objective wavelength components at different positions along the light paths. FIG. 4 shows a composite system 47 including a masked reflecting mirror for selecting the objective wavelength components and transparent optical media, each having a different thickness, placed on the light paths of the objective wavelength components. These optical systems such as shown in FIGS. 1–4 can also be applied to scanning laser microscopes.

Figure 5:
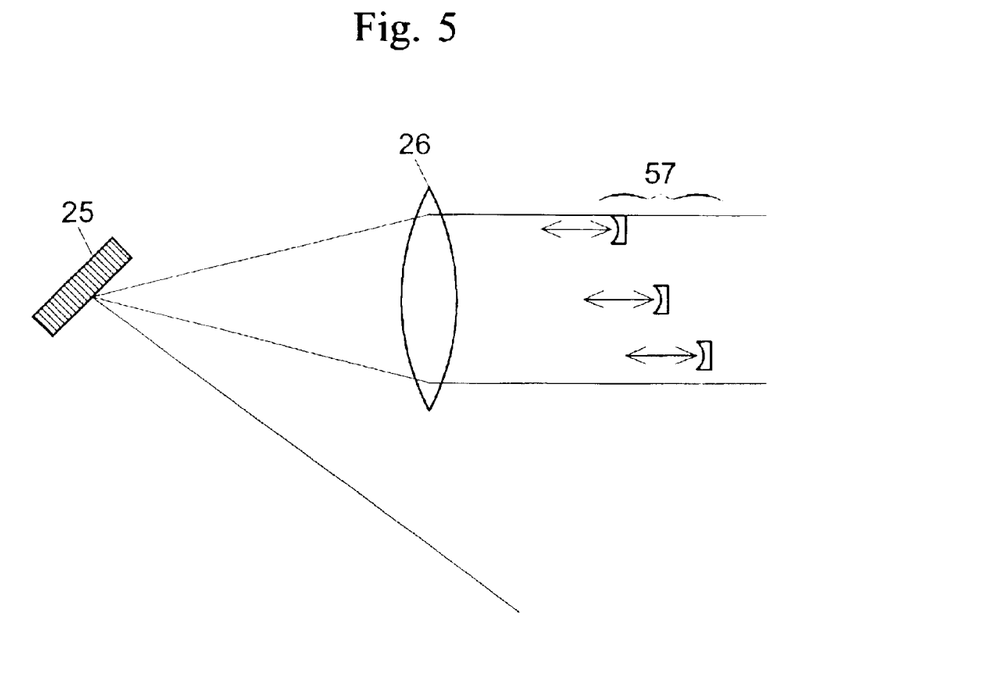
FIG. 5 shows the construction of the main part of an optical pulse generating system for giving chirps to the component optical pulse.

FIG. 5 shows a modified example of the system shown in FIG. 3, wherein all or a part of the small reflecting mirrors 57 are one-dimensionally curved. The curvature of the mirror 57 produces a diversion (or chirp) of the corresponding pulse component and a shift of its peak. This system may further include a mechanism for applying negative pressure to the back of the small reflecting mirror and for controlling the curvature by changing the negative pressure.

By the method according to the present invention, the continuous spectrum white light pulse is generated from an ultra-short optical pulse. This method provides such an ideal point source of light that allows a design of optical systems having high resolutions. Also, the method provides such a very bright light source that enables an analysis with little noise.

The method according to the present invention is particularly suitable for the analysis of bio-samples. That is, the method according to the present invention enables an almost simultaneous and real-time detection of a plurality of biological substances, such as proteins, because many biological materials are fluorescent or can be tagged with fluorescent probes. The combination of this method with a two- or three-dimensional scanning system of a microscope, for example, will produce two- or three-dimensional analytic images of the sample, and tracing of the image with time will enable an observation of motions or the like of the objective substances. Further, objective biological material that is not fluorescent can be detected by the method or system according to the present invention by labeling a protein or the like of the material with a fluorescent substance.

In the system according to the present invention, it is desirable to provide a mechanism for easily changing the objective wavelengths in addition to the mechanism for arbitrarily selecting the objective wavelengths as described above. For example, in developing a new fluorescent substance, it may be necessary to find the optimal excitation wavelength of the fluorescent substance. The optimal excitation wavelength will be found through testing some possible excitation frequencies one after another. This process, however, will take a long time if it is not easy to change the excitation wavelength. Another problem arises when the substances labeled with different fluorescent substances mingle in the sample. In this case, if the excitation wavelengths for all the fluorescent substances are simultaneously irradiated onto the sample, it will be very difficult to precisely locate each objective substance.

Taking account of the above problems, the system according to the first mode of the present invention further includes a shutter for arbitrarily passing or stopping the objective wavelength components selected by the wavelength selection device, and the reverse dispersing element generates the composite optical pulse by combining the objective wavelength components passing through the shutter.

In the system according to the second mode of the present invention, the wavelength selection device includes one or a plurality of wavelength selection elements for selecting only the objective wavelength components of the dispersed light, respectively, and an on/off mechanism for enabling or disabling each of the wavelength selection elements; and the reverse dispersing element generates the composite optical pulse by combining the objective wavelength components selected by the enabled wavelength selection elements.

In the system according to the third mode of the present invention, the wavelength selection mechanism includes a plurality of wavelength selection elements for selecting only the objective wavelength components of the dispersed light and a switching mechanism for selectively switching the plurality of wavelength selection elements, and the reverse dispersing element generates the composite optical pulse by combining the objective wavelength components selected by the wavelength selection elements selected by the switching mechanism.

The analysis with the first mode of the system is performed as follows. Before starting the analysis, the user should find out what frequencies should be selected to excite the one or a plurality of fluorescent substances under study. According to the present invention, since the excitation light is generated from an ultra-short optical pulse, a multiphoton excitation, such as two- or three-photon excitation, takes place. This fact should be taken into account in selecting the excitation frequencies.

The excitation light, or the pulse of the continuous spectrum white light, is dispersed into a spectrum, from which the wavelength selection device selects only one or a plurality of excitation wavelengths (objective wavelengths) of light. Examples of the wavelength selection device include an array of reflecting mirrors including a plurality of reflecting mirrors placed on the light paths of the objective wavelengths, a reflecting mirror covered with an absorption cover except for the parts that reflect the objective wavelength components.

Of all the objective wavelength components selected, only one or a plurality of objective wavelength components to be actually irradiated onto the sample are allowed to pass the shutter, and other objective wavelength components that may not be irradiated onto the sample at that moment are stopped by the shutter.

An example of the shutter is a mechanical shutter, such as a rotary disc shutter with a notch, or a plane shutter used in cameras. A liquid crystal shutter may also be used.

The objective wavelength components allowed to pass through the shutter are sent to the reverse dispersing element, which generates a composite optical pulse from the light. The reverse dispersing element may be provided separately from the dispersing element used for generating the spectrum, or the dispersing element may also be used as the reverse dispersing element.

The composite optical pulse generated as described above contains only excitation light pulses corresponding to the objective fluorescent substances. Therefore, of all the fluorescent substances in the sample, only the objective fluorescent substances are excited by the composite optical pulse. Further, by the first mode of the system, only the fluorescent substances necessary at the moment can be excited by properly changing the passing/stopping state of each shutter. By using the shutter, the objective wavelengths can be switched easily and quickly. Thus, it is easy to find the optimal excitation wavelength of a new fluorescent substance, or to separately detect each of a number of fluorescent substances mingling in the sample and study the distribution or behavior of each fluorescent substance.

In the second mode of the system, the wavelength selection device includes one or a plurality of wavelength selection elements (e.g. reflecting mirrors) for selecting only the objective wavelength components of the dispersed light, respectively, and an on/off mechanism enables or disables each of the wavelength selection elements. When a wavelength selection element is enabled, the wavelength corresponding to the wavelength selection element is sent to the reverse dispersing element, which generates a composite optical pulse containing the selected wavelength. On the other hand, when a wavelength selection element is disabled, the wavelength corresponding to that wavelength selection element is not sent to the reverse dispersing element, consequently the composite optical pulse does not contain that wavelength. Thus, with the on/off mechanism, the wavelength selection device can be controlled to arbitrarily change the combination of the wavelength components contained in the composite optical pulse.

In the third mode of the system, the wavelength selection device includes a plurality of wavelength selection elements for selecting only the objective wavelength components of the dispersed light, and a switching mechanism selectively switches the wavelength selection elements. This construction allows an arbitrary and easy change of the combination of wavelengths contained in the composite optical pulse.

The systems according to the first to third modes of the present invention are constructed to allow an arbitrary and easy change of the combination of wavelength components contained in the composite optical pulse. This feature provides the following preferable effects.

(1) In developing a new fluorescent substance, the optimal excitation wavelength can be found in a short time by testing through possible excitation wavelengths consecutively.

(2) Even when the substances labeled with fluorescent substances are mingled in the sample, each fluorescent substance can be precisely located by selecting the excitation wavelengths of the fluorescent substances consecutively so that each fluorescent substance is excited separately.

(3) When a plurality of excitation wavelength components are irradiated onto the sample, the different wavelength components interfere with each other, generating difference frequency components. The difference frequency components may excite fluorescent substances other than the objective ones, which causes a noise in the analysis. This problem can be solved with the system according to one of the first to third modes of the present invention by the following method: selectively exciting the fluorescent substances one after another, observing the fluorescence for each excitation, and combining all the observation results in the end. By such a method, the difference frequency components of light due to interference are eliminated, so that only the objective fluorescent substances can be observed with greatly reduced noise.

The method or system according to the present invention must further address the following problem. That is, the excitation wavelength of a fluorescent substance is not a single wavelength; it is excited by a certain small range of excitation wavelengths. Therefore, light of a wavelength different from the objective wavelength may cause an excitation. As explained above, when a plurality of wavelength components are irradiated onto the sample, the selected objective wavelength component might cause not only a two- or three-photon excitation of the objective fluorescent substance but also a linear excitation of fluorescent substances other than the objective ones. In this case, the fluorescence resulting from the excitation caused by the light other than the selected objective wavelength component will be a noise when detected by a detector.

Thus, it is desirable to improve the method or system according to the present invention so that an analysis can be performed with higher accuracy and less noise.

In view of the above object, the method according to the fourth mode of the present invention further includes:

a step where intensities of the plurality of objective wavelength components selected in step b) are modulated at different frequencies, and the plurality of objective wavelength components thus modulated are sent to step c);

a step where rays of fluorescence emitted from the sample by an excitation of the objective fluorescent substances in step d) is dispersed and detected for each objective wavelength; and a step where a detection signal of each ray of fluorescence is synchronously rectified at the frequency at which the intensity of the objective wavelength component corresponding to the fluorescence is modulated.

Further, the system according to the fifth mode of the invention further includes:

an intensity modulator for modulating intensities of the plurality of objective wavelength components, selected by the wavelength selection device, at different frequencies;

a fluorescence-dispersing element for dispersing rays of fluorescence emitted from the sample by an irradiation of the composite optical pulses by the irradiating optical system;

a detector for detecting the rays of fluorescence, dispersed by the fluorescence-dispersing element, for each objective wavelength component; and a synchronous rectifier for synchronously rectifying a detection signal of each ray of fluorescence, detected by the detector, at a frequency used in the intensity modulation of the objective wavelength component corresponding to the fluorescence.

In the analysis by the method according to the fourth mode of the invention or by the system according to the fifth mode of the invention, the user should first find out what frequencies should be selected to excite the plurality of fluorescent substances under study. According to the present invention, since the excitation light is generated from an ultra-short optical pulse, a multiphoton excitation, such as two- or three-photon excitation, takes place. This fact should be taken into account in the selection of the excitation frequencies.

The ultra-short optical pulse is repeatedly generated, from which a series of continuous spectrum white light pulses are generated. The continuous spectrum white light pulses are dispersed into spectrum, from which only the plurality of excitation wavelength components (or objective wavelength components) are selected. Examples of the method of selecting objective wavelength components include: placing reflecting mirrors only at such positions that correspond to the objective wavelengths; using a reflecting mirror covered with an absorption cover except for the parts that reflect the objective wavelength components; and using a mask designed to pass the dispersed light only at such parts that correspond to the objective wavelengths.

While the ultra-short optical pulses (i.e. the continuous spectrum white light pulses) are repeatedly generated, the intensities of the objective wavelength components selected as described above are modulated at different frequencies. The plurality of objective wavelength components, whose intensities have been modulated, are combined by the reverse dispersing element into a series of the composite optical pulses, which are irradiated onto the sample.

When the composite optical pulse is irradiated onto the sample, the fluorescent substances corresponding to the objective wavelength components in the sample are excited, and each fluorescent substance generates a ray of fluorescence. The sample simultaneously emits all the rays of fluorescence containing the plurality of objective wavelengths.

As described above, when a series of composite optical pulses are irradiated onto the sample, the sample correspondingly emits a series of fluorescent pulses. The fluorescent pulses are dispersed for each objective wavelength, and the intensity of the dispersed light is detected. The detection signal of a fluorescent pulse is synchronously rectified at the frequency used in the intensity modulation of the excitation light having the wavelength corresponding to the fluorescent pulse. The intensity of each wavelength component of the fluorescence changes at the same frequency as used in the intensity modulation of the excitation light corresponding to the wavelength component. Therefore, when the detection signal is synchronously rectified at the frequency, an objective signal component is extracted from the detection signal; otherwise a noise is extracted. Thus the signal component and the noise component are separately extracted from the detection signal.

Thus, by the method according to the fourth mode of the invention or by the system according to the fifth mode of the invention, the intensity of the objective excitation light is modulated, and the fluorescence is synchronously rectified at the modulation frequency. By such a process, objective fluorescence (objective component of signal) resulting from the excitation by the objective excitation light and other fluorescence (noise component of signal) resulting from excitation by other excitation light can be obtained separately.

The method and system according to the present invention are particularly suitable for the analysis of bio-samples especially for microscopes. That is, the method according to the present invention enables an almost simultaneous and real-time detection of a plurality of biological substances, such as proteins, because many biological materials are fluorescent. The combination of this method with a two- or three-dimensional scanning system, especially when used in a microscope, will produce two- or three-dimensional analytic images of the sample, and tracing of the image with time will enable an observation of motions or the like of the objective substances. Further, an objective biological material that is not fluorescent can be detected by the method or system according to the present invention by labeling a protein or the like of the material with a fluorescent substance.

As a result, not only the positions and distribution of the substances labeled with the fluorescent substances in the living body can be accurately determined but also a quantitative analysis of the labeled substances can be performed with high accuracy based on the intensity of the fluorescence. Combination of the present method or system with image analyzing techniques will make it possible to accurately find the amount, speed etc., of reactions of the labeled substances in the sample.

DETAILED DESCRIPTION OF A PREFERRED EMBODIMENT

Figure 6:
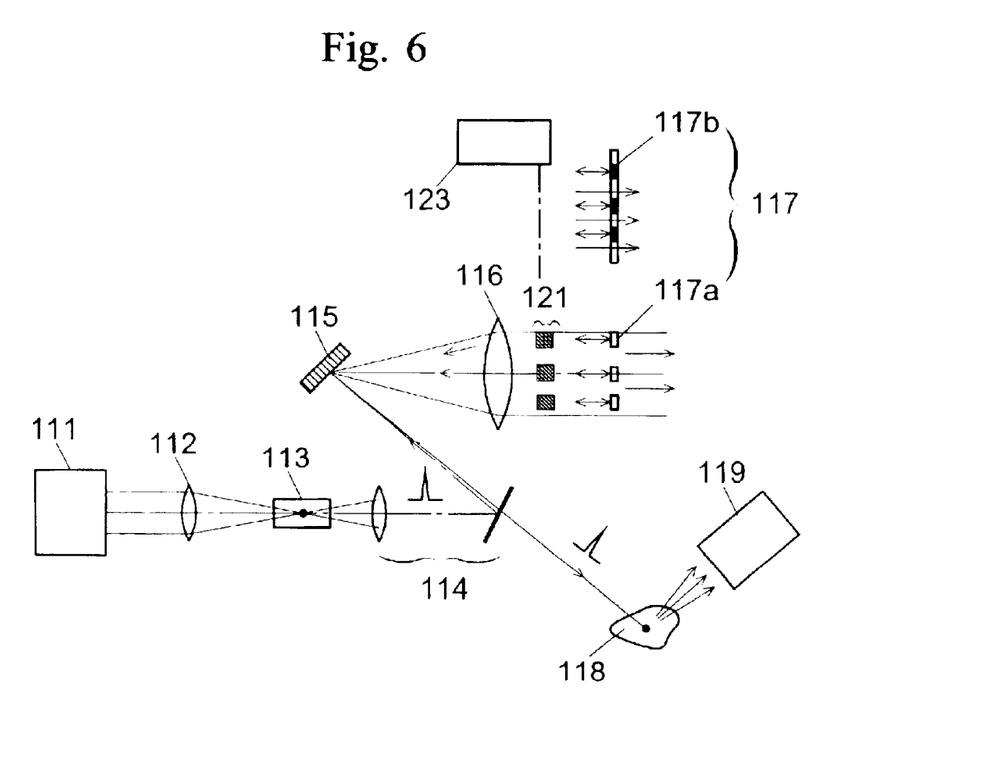
FIG. 6 shows the general construction of a fluorescent substance analyzer as an embodiment of the system according to the first mode of the present invention.
Figure 12:
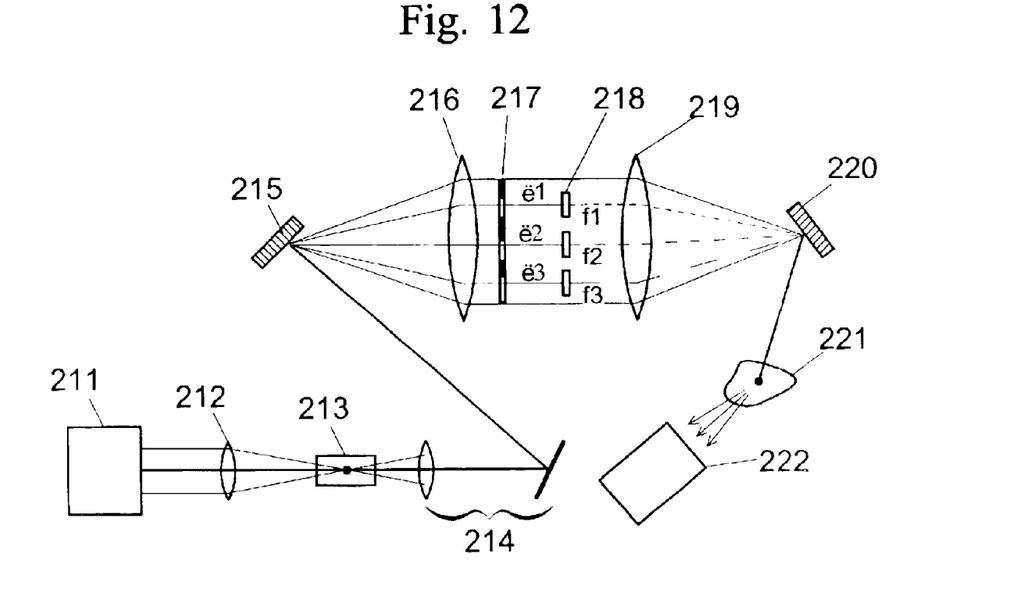
FIG. 12 shows the construction of a fluorescent substance analyzer as an embodiment of the fifth mode of the invention.

FIG. 6 shows a fluorescent substance analyzer as an embodiment of the first mode of the present invention. In FIG. 12, the light source 111 is, for example, an erbium-doped fiber laser, a mode-locked Ti:Sapphire laser or a mode-locked Cr:Forsterite laser, which generates an ultra-short optical pulse. The ultra-short optical pulse is converged by a first optical system 112 on a point in a transparent substance 113, such as water or quartz crystal. At the convergence point, a non-linear interaction occurs between the substance 113 and the ultra-short optical pulse, generating a continuous spectrum white light pulse. The continuous spectrum white light pulse enters a second optical system 114 including lenses, reflecting mirrors, etc. The second optical system 114 irradiates the light pulse onto a dispersing element 115, which in turn disperses the light pulse into a spectrum of light. The dispersed light enters a collimator 116, which sends the light to a wavelength selection device 117.

FIG. 6 shows two types of wavelength selection devices: the first type 117a includes small reflecting mirrors placed on the light paths of the objective wavelengths, and the second type 117b includes a reflecting mirror provided with light-absorbing parts at positions corresponding to wavelength components other than the objective ones.

Figure 7:
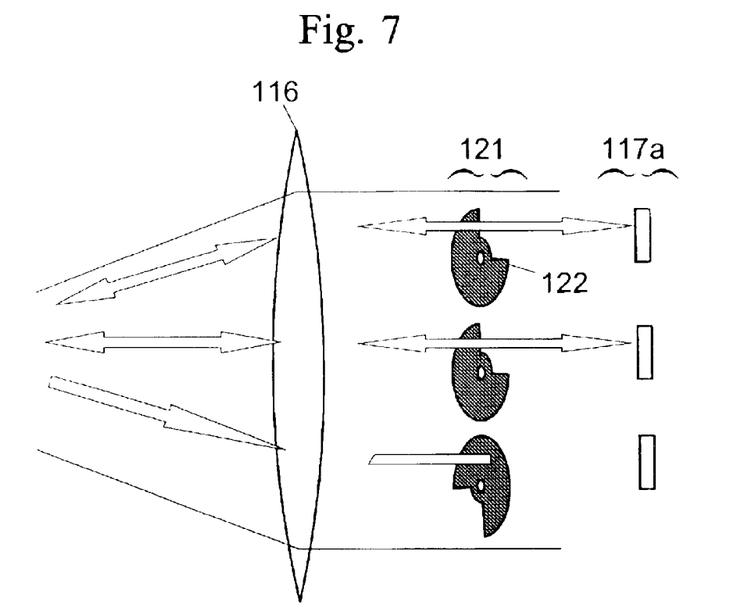
FIG. 7 shows the construction of the fluorescent substance analyzer in FIG. 6 at a part including a collimator and other elements placed behind it.

Shutters 121 are placed between the collimator 116 and the wavelength selection device 117. As shown in FIG. 7, the shutter 121 includes a rotary shutter unit 122 placed in front of the small reflecting mirror of the wavelength selection device 117a or in front of the reflecting part of the wavelength selection device 117b. Each rotary shutter unit can be arbitrary rotated by key operations on the operation unit 123 provided within easy reach of the user. A rotation of the rotary shutter switches the passing or stopping of light traveling along the light path corresponding to the rotary shutter. The operation unit 123 may be constructed with simple switches. Otherwise, a controller (often a personal computer) for controlling the general operation of the fluorescent substance analyzer may be made to function as the operation unit 123.

Only the wavelength components selected by the wavelength selection device 117 and allowed to pass through the shutters 121 return through the collimator 116 to the dispersing element 115, which combines the wavelength components into an ultra-short optical pulse. The ultra-short optical pulse is irradiated onto the sample 118 to excite a plurality of objective substances. The fluorescence resulting from the excitation is detected by a detector 119.

Thus, with the fluorescent substance analyzer of this embodiment, the user can easily change the combination of the wavelength components contained in the composite optical pulse irradiated onto the sample 118 by operating the operation unit 123 provided within easy reach of the user.

When a plurality of wavelength components are selected to pass through the shutters 121, the composite optical pulse irradiated onto the sample contains the selected plurality of wavelength components. In this case, the components of the composite optical pulse may possibly interfere with each other, generating difference frequency components due to the non-linear effect. The difference frequency components thus generated may excite fluorescent substances other than the objective ones, which becomes a noise in the analysis. Bearing this in mind, it is preferable to make the light path lengths of the objective wavelength components different from each other. By this construction, the component optical pulses selected by the shutters 121 are contained in the composite optical pulse with time differences, so that the difference frequency components and the above noise are prevented.

Figure 10:
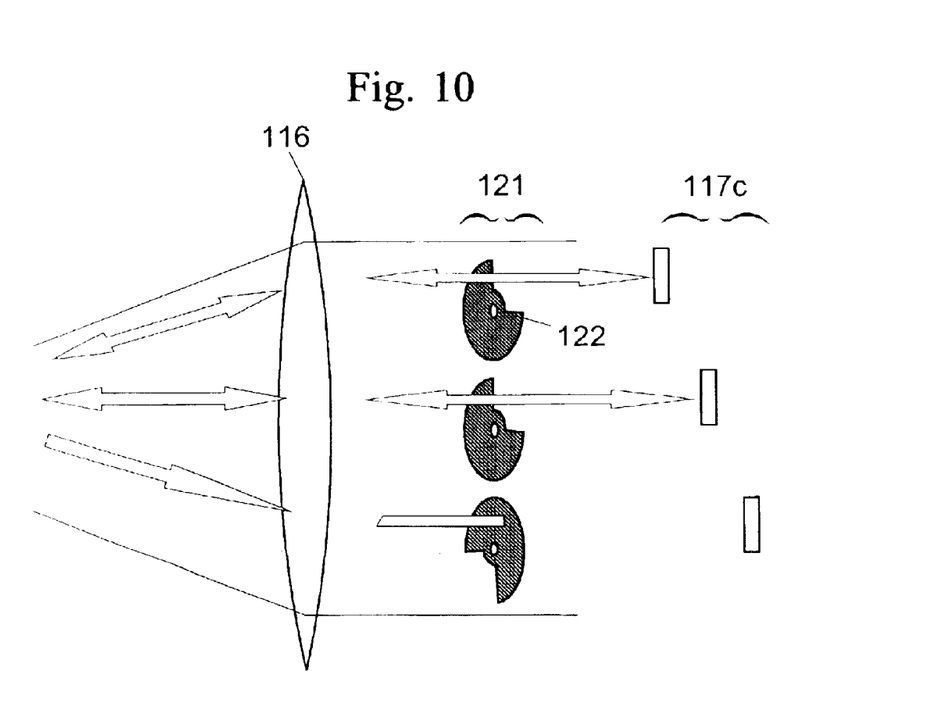
FIG. 10 shows the first modification of the embodiment of the first mode.
Figure 11:
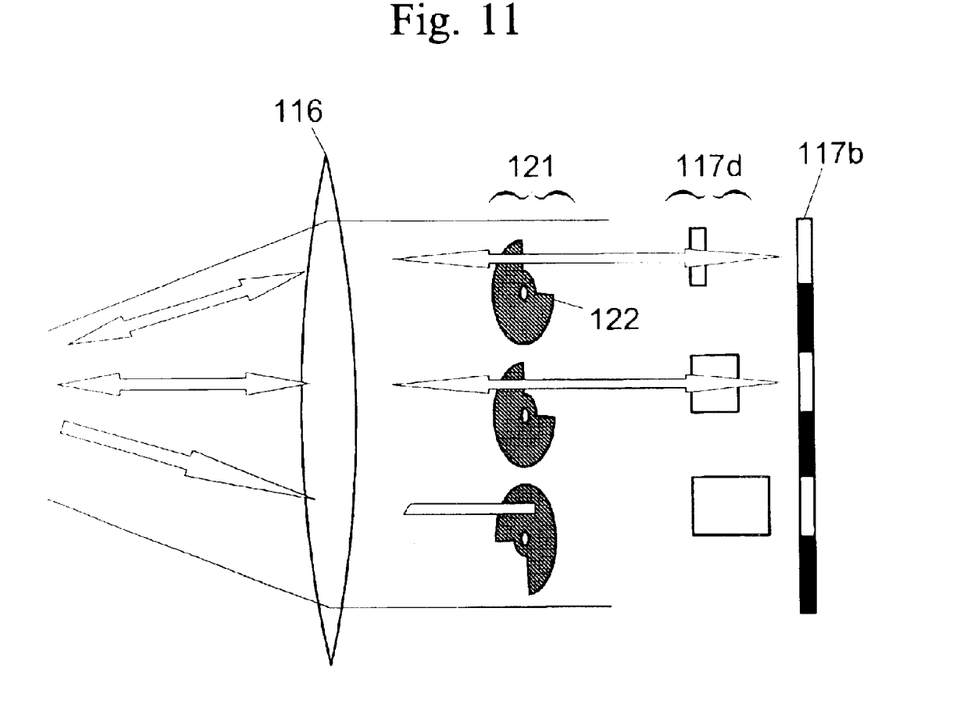
FIG. 11 shows the second modification of the embodiment of the first mode.

FIGS. 10 and 11 show examples of the above-described construction. The example shown in FIG. 10 includes small reflecting mirrors 117 placed on the light paths of the objective wavelength components at different positions along the light paths to make the light path lengths different. The example shown in FIG. 11 includes transparent optical media 117d placed on the light paths of the objective wavelength components defined by a selective mirror type of wavelength selection device 117b. The optical media have different thickness (i.e. the dimension in the direction of the light path) to optically change the light path lengths. The optical media should preferably be made from a material having a large refractive index. In either of the cases, the rotary shutter unit 122 is placed on each light path to constitute the shutter 121.

Figure 8:
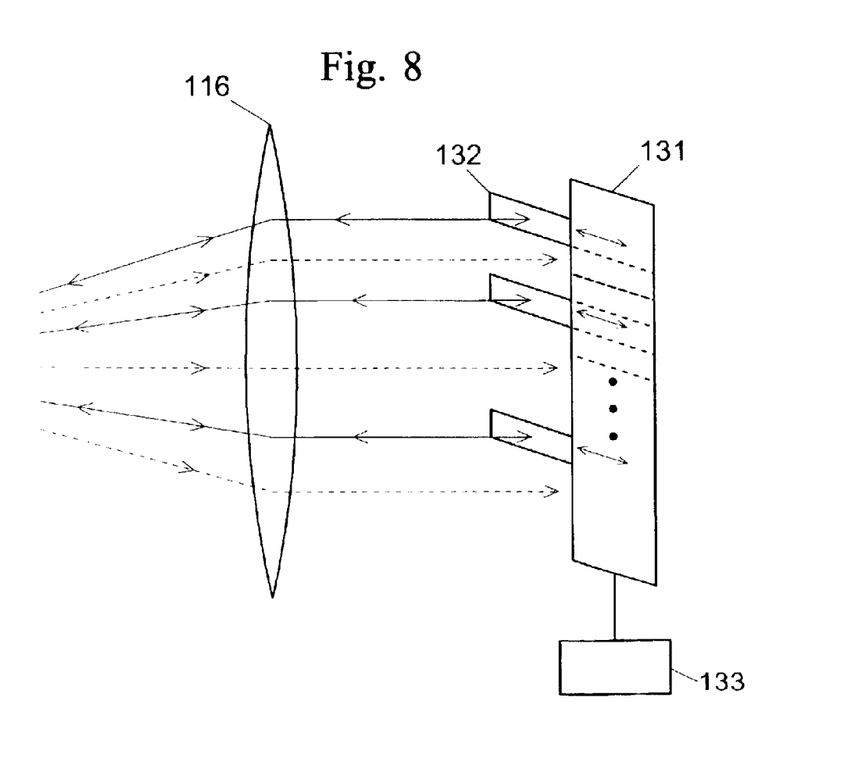
FIG. 8 shows the construction of a fluorescent substance analyzer as an embodiment of the second mode of the present invention at a part including a collimator and other elements placed behind it.

A fluorescent substance analyzer as an embodiment of the second mode of the invention is described. FIG. 6 shows the general construction of the analyzer, and FIG. 8 shows a part of the analyzer including the collimator 116 and other elements placed behind it. The wavelength selection device 131 includes a number of small mirrors 132 placed corresponding to the light paths of the wavelengths of the dispersed light. On receiving a command signal from the operation unit 133, the wavelength selection device 131 projects the small mirror 132 into the corresponding light path. In the light path into which the small mirror 132 is projected, the light having the corresponding wavelength is reflected by the small mirror 132 back to the collimator 116, and the dispersing element 115 combines the reflected light into an ultra-short optical pulse. In the other light paths, the light is not reflected back to the dispersing element 115, so that the composite optical pulse does not contain the wavelength components corresponding to those light paths. Thus, with the system of this embodiment, the wavelength components contained in the composite optical pulse irradiated onto the sample 118 can be arbitrarily selected by giving proper commands through the operation unit 133.

Figure 9:
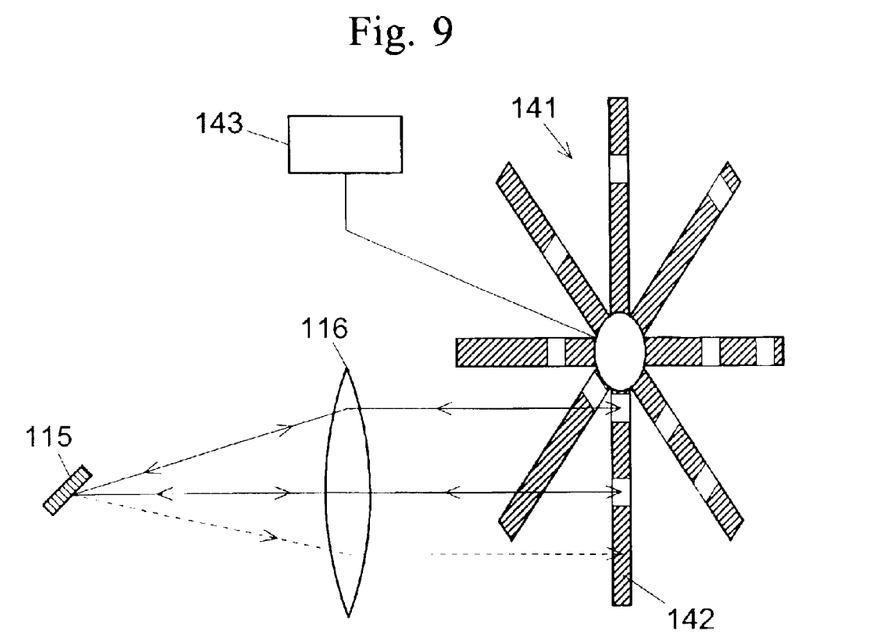
FIG. 9 shows the construction of a fluorescent substance analyzer as an embodiment of the third mode of the present invention at a part including a collimator and other elements placed behind it.

A fluorescent substance analyzer as an embodiment of the third mode of the invention is described. FIG. 6 shows the general construction of the analyzer, and FIG. 9 shows a part of the analyzer including the collimator 116 and other elements placed behind it. The analyzer in this embodiment has a plurality of wavelength selection devices 142 and a switching mechanism 141 for selectively switching the wavelength selection devices 142. Each wavelength selection device 142 has light-absorbing parts and reflection parts selectively formed as in the wavelength selection device 117b shown in FIG. 6. The switching mechanism 141 in FIG. 9 is a rotary mechanism for selectively placing the wavelength selection devices 142 on the light paths. A parallel translation mechanism may also be used to construct the switching mechanism 141. Commands for the switching operation are given through the operation unit 143.

FIG. 12 shows a fluorescent substance analyzer as an embodiment of the fifth mode of the invention. In FIG. 12, the light source 211 is, for example, an erbium-doped fiber laser, a mode-locked Ti:Sapphire laser or a mode-locked Cr:Forsterite laser, which periodically generates a series of ultra-short optical pulses at substantially regular time intervals. As explained above, the width of the ultra-short optical pulse is of the femtosecond ($10^{-15}$ second) order, and the frequency of generation of the pulses is about 80 to 100 MHz.

The ultra-short optical pulses generated by the light source 211 are converged by the first optical system 212 on a point in a transparent substance 213, such as water or quartz crystal. At the convergence point, a non-linear interaction occurs between the substance 213 and the ultra-short optical pulses, generating a series of continuous spectrum white light pulses. The continuous spectrum white light pulses enter a second optical system 214 including lenses, reflecting mirrors, etc. The second optical system 214 irradiates the light pulses onto a dispersing element 215, which in turn disperses the pulse into a spectrum of light. A collimator 216 sends the dispersed light to a wavelength selection device 217, which selects a plurality of excitation wavelength components ($\lambda 1$, $\lambda 2$ and $\lambda 3$) for exciting objective fluorescent substances.

Figure 13:
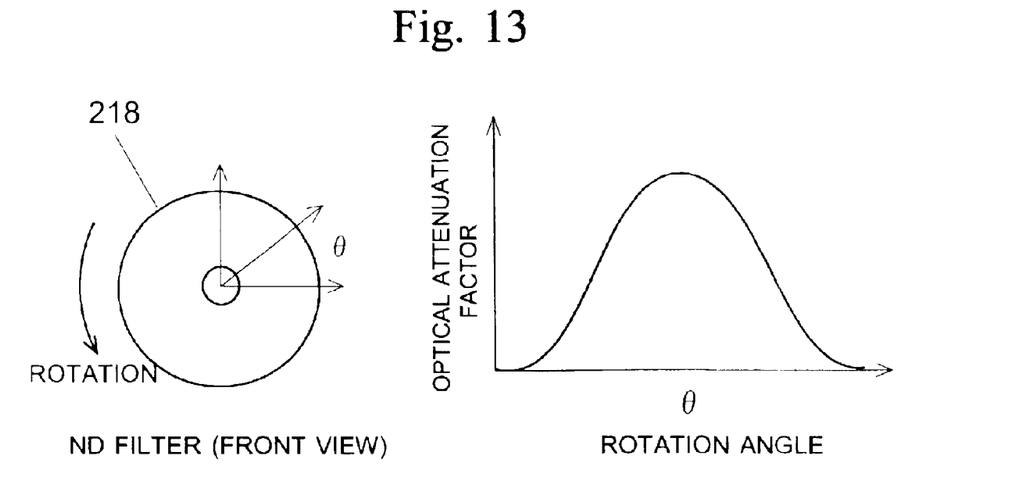
FIG. 13 shows a neutral density (ND) filter used in the fluorescent substance analyzer in FIG. 12 and a graph representing the relationship between the rotation angle and the optical attenuation factor.
Figure 14:
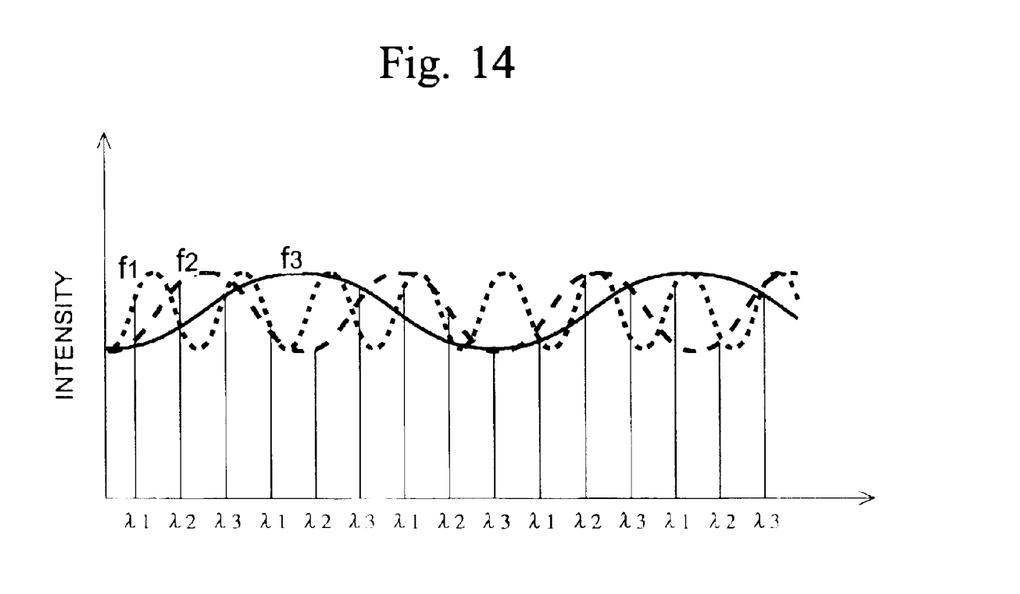
FIG. 14 is a graph showing the state of intensity modulations of excitation wavelength components $\lambda 1$, $\lambda 2$ and $\lambda 3$.

After passing through the wavelength selection device 217, the selected excitation wavelength components $\lambda 1$, $\lambda 2$ and $\lambda 3$ enter an intensity modulator 218, which modulates the intensities of the excitation wavelength components at different frequencies f1, f2 and f3. The intensity modulator 218 includes a rotary disc type of neutral density (ND) filter provided for each wavelength component. Each ND filter is designed so that its optical attenuation factor changes with the rotation angle, as shown in FIG. 13. The ND filters are rotated at different rotation speeds, whereby the intensities of the excitation wavelength components are modulated at different frequencies f1, f2 and f3 corresponding to the rotation speeds of the ND filters. FIG. 14 shows the state of intensity modulations of the excitation wavelength components. The excitation light of wavelength $\lambda 1$, whose intensity is modulated at frequency f1, presents a sinusoidal change of intensity at frequency f1. Similarly, the intensities of the wavelength components $\lambda 2$ and $\lambda 3$ are modulated at frequencies f2 and f3, respectively.

The excitation wavelength components $\lambda 1$, $\lambda 2$ and $\lambda 3$ are irradiated by a converging optical system 219 onto a reverse dispersing element 220, which combines the wavelength components into an ultra-short optical pulse. The ultra-short optical pulse is irradiated onto the sample 221.

As described above, the light source 211 generates ultra-short optical pulses at the frequency of 80 to 100 MHz. Therefore, the composite optical pulses irradiated onto the sample are generated at the same frequency. In the sample 221, the plurality of excitation wavelength components contained in the composite optical pulses excite a plurality of objective fluorescent substances, each of which emits a ray of fluorescence. Rays of fluorescence generated by the fluorescent substances are simultaneously emitted from the sample 211 and detected by a fluorescence detection system 222.

Figure 15:
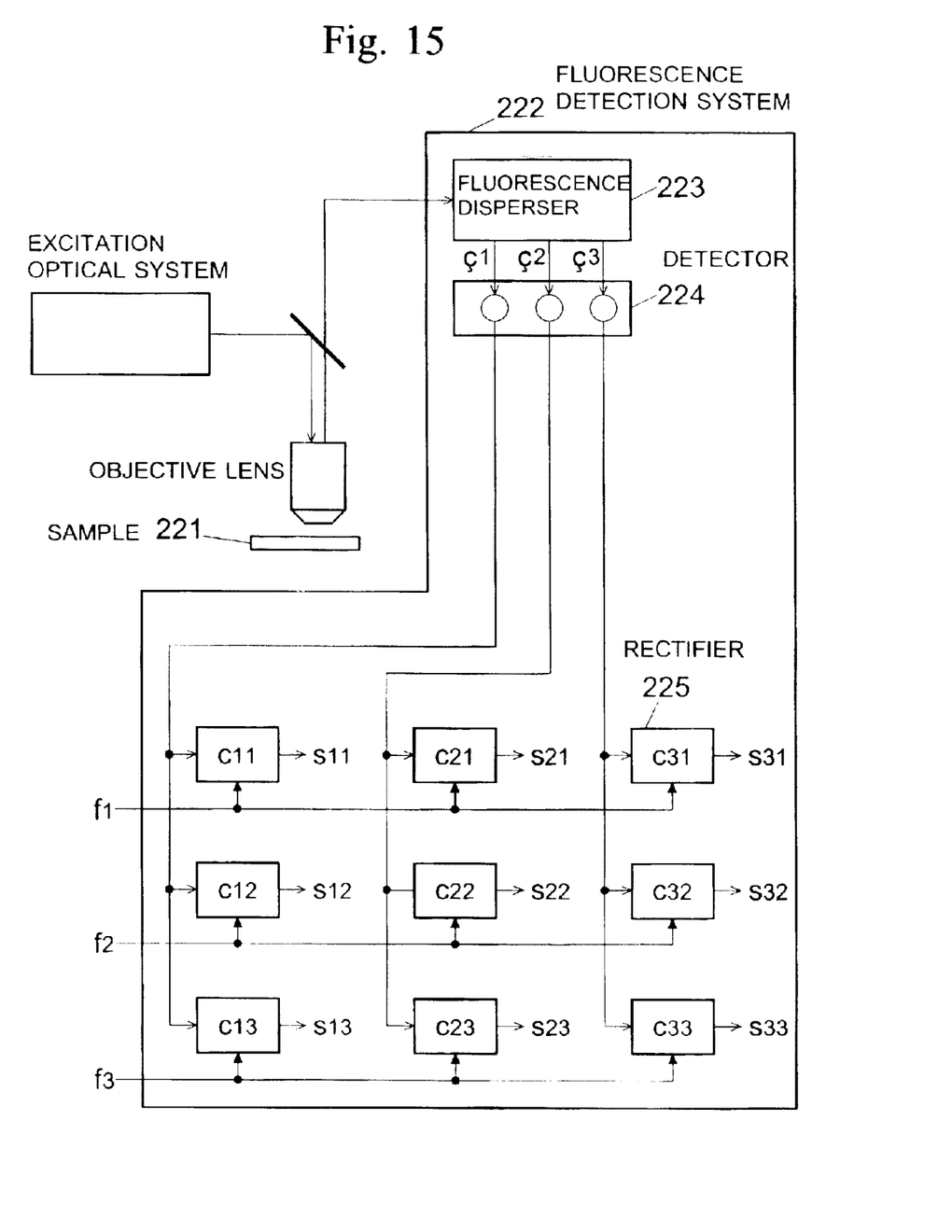
FIG. 15 shows the construction of a fluorescence detection system.

The operation of the fluorescence detection system 222 is described with reference to FIG. 15. The fluorescence emitted from a sample 221 is dispersed by a fluorescence-dispersing device 223 into objective fluorescence wavelength components $\eta 1$, $\eta 2$ and $\eta 3$. The intensities of the dispersed fluorescence components $\eta 1$, $\eta 2$ and $\eta 3$ are detected by a detector 224.

The detector 224 outputs detection signals corresponding to the fluorescence components $\eta 1$, $\eta 2$ and $\eta 3$, and the detection signals are synchronously rectified at the intensity modulation frequencies f1, f2 and f3 of the excitation wavelength components, respectively. Synchronous rectification is performed with an array of rectifiers 225. In FIG. 15, three modulation frequencies f1, f2 and f3 are used because there are three excitation wavelengths (and fluorescence wavelengths) $\eta 1$, $\eta 2$ and $\eta 3$. Accordingly, nine rectifiers c11–c33 are employed.

For example, the detection signal of the fluorescence of wavelength $\eta 1$ is sent to the rectifiers c11, c12 and c13, which synchronously rectify the signal at frequencies f1, f2 and f3, respectively. Since the fluorescence of wavelength $\eta 1$ is generated by the excitation wavelength component $\lambda 1$ whose intensity is modulated at frequency f1, the detection signal of the fluorescence of wavelength $\eta 1$ presents a periodical intensity change at frequency f1. Therefore, the output signal s11 of the rectifier c11 performing the synchronous rectification at frequency f1 contains information about only the fluorescence emitted from the objective fluorescent substance. On the other hand, the output signals s12 and s13 of the other two rectifiers c12 and c13 performing the synchronous rectifications at frequencies f2 and f3, respectively, contain information about other fluorescence resulting from excitations caused by the excitation wavelength components $\lambda 1$ and $\lambda 2$ corresponding to the frequencies f2 and f3. Thus, from the same fluorescence, the objective output signal s11 and other output signals s12 and s13 regarded as a noise are separately produced.

As regards the fluorescence of wavelength $\eta 2$, the rectifier c22 performing the synchronous rectification at frequency f2 outputs the objective signal s22, and other rectifiers c21 and c23 performing the synchronous rectifications at frequencies f1 and f3, respectively, output noise signals s21 and s23. A similar explanation also applies to the case of the fluorescence of wavelength η3.

As described above, the fluorescent substance analyzer of this embodiment can detect only the objective fluorescence resulting from the excitation caused by the excitation wavelength component corresponding to the objective fluorescent substance, while removing detection signals of undesired fluorescence caused by other excitation wavelength components. Thus, the sample can be analyzed with high accuracy.

What is claimed is:

1. A method of analyzing a sample, comprising:
   a) a step where a continuous spectrum white light pulse generated from an ultra-short optical pulse is dispersed into a spectrum of light by a dispersing element;
   b) a step where a plurality of objective wavelength components are selected from the dispersed light;
   c) a step where the plurality of objective wavelength components are combined by a reverse dispersing element into a composite optical pulse containing the objective wavelength components; and
   d) a step where the composite optical pulse is irradiated onto the sample to excite a plurality of objective fluorescent substances corresponding to the plurality of objective wavelength components.

2. The method according to claim 1, wherein the selected plurality of objective wavelength components have different light path lengths so that the composite optical pulse contains component optical pulses corresponding to the objective wavelengths with time differences.

3. The method according to claim 2, wherein reflecting mirrors are placed on the light paths of the objective wavelength components at different positions along the light paths to make the light path lengths of the plurality of objective wavelength components different.

4. The method according to claim 2, wherein transparent optiesi media, each having a different thickness, are placed on the light paths of the objective wavelength components to make the light path lengths of the plurality of objective wavelength components different.

5. The method according to claim 2, wherein at least one of the objective wavelength components is chirped.

6. A system for analyzing a sample, comprising:
   a) a light source for generating a continuous spectrum white pulse light using an ultra-short optical pulse:
   b) a dispersing element for dispersing a continuous spectrum white light pulse generated from an ultra-short optical pulse into a spectrum of light;
   c) a wavelength selection device for selecting a plurality of objective wavelength components contained in the dispersed light;
   d) a reverse dispersing element for combining the selected plurality of objective wavelength components into a composite optical pulse; and
   e) an irradiating optical system for irradiating the composite optical pulse onto the sample.

7. The system according to claim 6, further comprising a plurality of mirrors placed on the light paths of the plurality of objective wavelength components of the dispersed light at different positions along the light paths.

8. The system according to claim 7, wherein at least one mirror has a non-planer reflection surface to chirp the objective wavelength component corresponding to the mirror.

9. The system according to claim 6, further comprising transparent media, each having a different thickness, placed on the light paths of the plurality of objective wavelength components of the dispersed light.

10. The system according to claim 9, wherein at least one medium has a non-planer end surface to chirp the objective wavelength component corresponding to the medium.

11. The system according to claim 6, further comprising a shutter for arbitrarily passing or stopping the objective wavelength components selected by the wavelepgth selection device, wherein the reverse dispersing element generates the composite optical pulse by combining the objective wavelength components passing through the shutter.

12. The system according to claim 6, wherein:
   the wavelength selection device includes one or a plurality of wavelength selection elements for selecting only the objective wavelength components of the dispersed light, respectively, and an on/off mechanism for enabling or disabling each of the wavelength selection elements; and
   the reverse dispersing element generates the composite optical pulse by combining the objective wavelength components selected by the enabled wavelength selection elements.

13. The system according to claim 6, wherein:
   the wavelength selection mechanism includes a plurality of wavelength selection elements for selecting only the objective wavelength components of the dispersed light and a switching mechanism for selectively switching the plurality of wavelength selection elements; and
   the reverse dispersing element generates the composite optical pulse by combining the objective wavelength components selected by the wavelength selection elements selected by the switching mechanism.

14. The method according to claim 1, further comprising
   a step wherein intensities of the plurality of objective wavelength components selected in step b) are modulated at different frequencies, and the plurality of objective wavelength components modulated are sent to step c);
   a step wherein rays of fluorescence emitted from the sample by an excitation of the objective fluorescent substances in step d) are dispersed and detected for each objective wavelength; and a step wherein a detection signal of each ray of fluorescence is synchronously rectified at the frequency at which the intensity of the objective wavelength component corresponding to the fluorescence is modulated.

15. The system according to claim 6, further comprising
   an intensity modulator for modulating intensities of the plurality of objective wavelength components, selected by the wavelength selection device, at different frequencies;
   a fluorescence-dispersing element for dispersing rays of fluorescence emitted from the sample by an irradiation of the composite optical pulses by the irradiating optical system;
   a detector for detecting the rays of fluorescence, dispersed by the fluorescence-dispersing element, for each objective wavelength component; and
   a synchronous rectifier for synchronously rectifying a detection signal of each ray of fluorescence, detected by the detector, at a frequency used in the intensity modulation of the objective wavelength component corresponding to the fluorescence.

16. The system according to claim 15, wherein the intensity modulator includes disc type rotary filters whose optical attenuation factor changes with its rotation angle.

17. A scanning laser microscope comprising:
a) a light source for generating a continuous spectrum white light pulse using an ultra-short optical pulse;
b) a dispersing element for dispersing the continuous spectrum white light pulse into a spectrum of light;
c) a wavelength selection device for selecting a plurality of objective wavelength components contained in the dispersed light;
d) a reverse dispersing element for combining the selected plurality of objective wavelength components into a composite optical pulse; and
e) a scanning optical system for scanning the composite optical pulse on a sample.

18. The scanning laser microscope according to claim 17, further comprising a plurality of mirrors placed on the light paths of the plurality of objective wavelength components of the dispersed light at different positions along the light paths.

19. The scanning laser microscope according to claim 18, wherein at least one mirror has a non-planer reflection surface to chirp the objective wavelength component corresponding to the mirror.

20. The scanning laser microscope according to claim 17, further comprising a plurality of transparent media, each having a different thickness, placed on the light paths of the plurality of objective wavelength components of the dispersed light.

21. The scanning laser microscope according to claim 20, wherein at least one medium has a non-planer end surface to chirp the objective wavelength component corresponding to the medium.

22. The scanning laser microscope according to claim 17, further comprising a shutter for arbitrarily passing or stopping the objective wavelength components selected by the wavelength selection device, wherein the reverse dispersing element generates the composite optical pulse by combining the objective wavelength components passing through the shutter.

23. The scanning laser microscope according to claim 17, wherein:
the wavelength selection device includes one or a plurality of wavelength selection elements for selecting only the objective wavelength components of the dispersed light, respectively, and an on/off mechanism for enabling or disabling each of the wavelength selection elements; and
the reverse dispersing element generates the composite optical pulse by combining the objective wavelength components selected by the enabled wavelength selection elements.

24. The scanning laser microscope according to claim 17, wherein:
the wavelength selection mechanism includes a plurality of wavelength selection elements for selecting only the objective wavelength components of the dispersed light and a switching mechanism for selectively switching the plurality of wavelength selection elements; and
the reverse dispersing element generates the composite optical pulse by combining the objective wavelength components selected by the wavelength selection elements selected by the switching mechanism.

* * * * *